United States Patent [19]

Krieg et al.

[11] Patent Number: 5,361,912

[45] Date of Patent: Nov. 8, 1994

[54] APPARATUS AND PROCESS FOR CLASSIFYING THE CONTENTS OF NON-DISPOSABLE BEVERAGE BOTTLES AND CONTAINERS

[75] Inventors: Gunther Krieg; Karl Koukolitschek, both of Karlsruhe; Wilfried Maier, Sulzfeld, all of Germany

[73] Assignee: Prof. Dr. Ing. Gunther Krieg, Karlsruhe, Germany

[21] Appl. No.: 182,349

[22] Filed: Jan. 18, 1994

Related U.S. Application Data

[63] Continuation of Ser. No. 21,594, Feb. 24, 1993, abandoned.

[30] Foreign Application Priority Data

Feb. 25, 1992 [DE] Germany .............................. 4205722

[51] Int. Cl.$^5$ ................................................ B07C 5/00
[52] U.S. Cl. .................................... 209/524; 209/582; 209/587; 356/240; 356/448
[58] Field of Search ............... 209/524, 527, 577, 578, 209/581, 582, 587–589; 73/53.01, 61.41; 250/223 B, 565, 341; 356/240, 427, 448

[56] References Cited

U.S. PATENT DOCUMENTS

| | | | |
|---|---|---|---|
| 3,917,947 | 11/1975 | Fenton | 209/524 X |
| 4,158,625 | 6/1979 | Takahashi | 209/524 |
| 4,557,386 | 12/1985 | Buckley et al. | 209/527 X |
| 4,605,851 | 8/1986 | Ometz et al. | 356/427 X |
| 4,766,551 | 8/1988 | Begley | 356/448 X |
| 4,858,768 | 8/1989 | Plester | 209/577 X |
| 4,902,137 | 2/1990 | Krieg et al. | 356/240 X |
| 4,998,824 | 3/1991 | Littlejohn et al. | 209/582 X |
| 5,002,397 | 3/1991 | Ingrum et al. | 209/582 X |

FOREIGN PATENT DOCUMENTS

| | | |
|---|---|---|
| 0254879 | 6/1987 | European Pat. Off. . |
| 4038993 | 12/1990 | Germany . |
| WO88/00862 | 2/1988 | WIPO . |

OTHER PUBLICATIONS

Techmisches Messen 58 (1991) 3 © R. Oldenbourg Verlag "Produktinformation –Meβumformer-Interface".

"A Novem Infrared Spectrometer Using a Linear Array Detector", Hugh H. Richardson, et al.–1369 Applied Spectroscopy 44 No. 5 Jun. 1990.

"Signal processing for an infrared detector", by M. A. Yound, et al., Review of Scientific Instruments, 60 No. 9 Sep. 1989.

"Characterization of a Computerized Photodiode Array Spectrometer for gas Chromatography–Atomic Emission Spectrometry" by James J. Sullivan, et al.–Analytical Chemistry–62 No. 10 May 1990.

"A Photodiode-Array-Based Near-Infrared Spectrophotometer for the 600–1100 nm Wavelength Region" by David M. Mayes, et al.–1369 Applied Spectroscopy 43 No. 1 Jan. 1989.

*Primary Examiner*—D. Glenn Dayoan
*Attorney, Agent, or Firm*—Antonelli, Terry, Stout & Kraus

[57] ABSTRACT

The invention relates to a process and an apparatus for the selective on-line identification and distinguishing of pollutants and contents in bottles/containers in filling systems in the beverage or drinks industry using the absorption, reflection and scattering of electromagnetic waves from the UV to the microwave range, characterized in that characteristic value pairs/ranges of wavelength and amplitude are used for identification and distinguishing.

16 Claims, 6 Drawing Sheets

APPARATUS AND PROCESS FOR CLASSIFYING THE CONTENTS OF NON-DISPOSABLE BEVERAGE BOTTLES AND CONTAINERS

This is a continuation division of application Ser. No. 08/021,594, filed Feb. 24, 1993, now abandoned.

DESCRIPTION

The invention relates to an apparatus and a process for classifying the contents of non-disposable beverage bottles and containers. particularly for food industry products, but also those of the chemical industry. Apart from the problem solved in U.S. patent application No. 905,470 now U.S. Pat. No. 5,305,887 and German patent application P 4203274.1 of pollutant identification and classification linked with the sorting out e.g. from filling lines of bottles/containers contaminated with pollutants, the economic aspect is of major significance. It requires that the products belonging to the particular non-disposable bottle/container do not lead to a discharge. In the beverage or drinks industry this means that e.g. petrol or diesel-contaminated bottles/containers are discharged, but that drink contents such as e.g. citrus flavours or harmless fermentation products such as e.g. ethanol do not lead to a discharge. Thus, e.g. the content limonene, which is in part contained in higher concentrations in soft or sweet drinks is detected as a "good" substance and this also applies with regards to ethanol, provided that the concentrations are relatively low in accordance with the fermentation processes taking place.

However, to make the problem posed more difficult the presence of ethanol must lead to a discharge if the concentrations are so high that it is not possible to exclude that these are not pure fermentation products, but instead detergents or spirit, which can lead to flavour falsifications on refilling the bottle/container with the new product. The same applies in connection with the contamination with cleaning agents which, for odour concealment purposes, are mixed with high limonene percentages and due to the cleaning chemical constituents must be removed from the process.

The considerable complication of the set problem compared with U.S. patent application No. 905,470 is inter alia that above a given concentration a substance classified as "good" must lead to a "bad" characterization and therefore to a discharge.

WO 88/00862 discloses processes for determining contaminated and uncontaminated containers, which do not give satisfactory results inconnection with the above set problem.

For solving this problem according to the invention the sums are formed from positive functions of differences between associated ordinate values of the actual on-line measured spectra and those in the memory and the substance having the smallest sum value or total is considered to be detected.

According to a preferred development the "good" and "bad" substances identified by special "fingerprints" according to U.S. patent application No. 905,470 are in each case detected as belonging to one or other category and thresholds are used as a criterion for non-discharge or discharge. These thresholds are chosen in such a way that for concentrations above or below preselected concentrations a discharge does or does not take place.

In the special case of citrus flavours, e.g. limonene this means that according to the invention firstly the citrus component is detected as a "good" substance and in the next process stage detection takes place to establish whether the concentration is below a threshold $S_1$, which is e.g. so chosen that it is not exceeded for soft drinks of all types and does not lead to a discharge.

However, if the limonene concentration is above $S_2$, an additional check is made according to the invention to establish whether e.g. limonene-mixed cleaning agents are present. On exceeding a threshold $S_2$, which is below the limonene concentration of standard cleaning agents, the particular bottle/container is discharged in accordance with the present invention. The same applies e.g. for ethanol, which is formed in small concentrations during the fermentation of soft drinks and remains in the drink filling line when below the threshold $S_3$, but on exceeding the threshold $S_4$ leads to a discharge, because e.g. spirit, highly concehtrated alcoholic liquors, wine, etc. can be present as ethanol-containing, flavour-falsifying substances.

To be able to carry out the classification according to the invention with a probability bordering on certainty in the constituent groups:

| | |
|---|---|
| "true pollutants", | e.g. acetone, petrol, diesel, methanol, xylene, benzene, toluene, etc. and mixtures thereof, |
| "camouflaged pollutants" | such as limonene-mixed cleaning agents, ethanol-mixed detergents, etc. |
| "bottle/container-specific products" | such as e.g. soft drinks, mineral waters fruit juices, etc., |

According to the invention effective measures are provided for selective substance detection. In addition, the invention proposes processes and apparatuses for the concentration determination of the aforementioned components, i.e. for precise classification into "bottle/container-specific products" below the threshold $S_1$, $S_3$ and including fermentation products thereof and "true" or "camouflaged" pollutants above the threshold $S_2$, $S_4$.

Building up on the technical teaching of U.S. patent application No. 905,470, the pollutant detection is decisively improved according to the invention, in that the substance-specific spectra obtained by spectral processes in the ultraviolet, visible, infrared and microwave spectral ranges, undergo a novel evaluation process. The latter is based on the comparison of the actual spectra measured on a bottle/container sample with spectra filed in a memory taking place in such a way that according to the invention a comparison is made to establish whether the actually measured and stored values coincide as regards:

the positions of the maxima and minima on the wavelength scale, the half-intensity widths, i.e. the wavelength intervals at half the height, the base widths, i.e. the wavelength intervals within which there is a spectrum, the amplitude ratios of the maxima present, the amplitude ratios of the minima present, the amplitude ratios of maxima and minima.

As a result of these measures it is ensured that the necessary on-line evaluation is made possible for the first time with the high bottle capacities of up to 50,000 bottles per hour in the drinks industry using a single sensor system and at the same time with an acceptable computing expenditure, i.e. greatly reduced computation activity.

As the incorrect discharge or elimination of bottles, i.e. without any need for the same, leads to additional manual work in the drinks industry causing inadmissible additional costs, in order to avoid these costs the invention provides further measures which, in conjunction with the aforementioned measures, increase to almost 100% the reliability of selective substance detection. According to the invention the spectra are scanned in point pairvise manner and the following processes are used in the comparison between the actually measured and stored spectra:

determination of the sum of the standard deviations of all the individual points, determination of the sum of the differences of all the individual points.

The substance within the numerous stored substances is considered to be detected in which the above quantities have a minimum and in which the maximum is below a number to be set by the plant operator.

According to a further development of the invention the quotients between the actual and the stored spectra are formed and the resulting quotient function evaluated.

BRIEF DESCRIPTION OF THE DRAWINGS

The invention is described in greater detail hereinafter relative to the drawings, wherein show.

DETAILED DESCRIPTION OF THE PREFERRED EMBODIMENT

Figure 1:
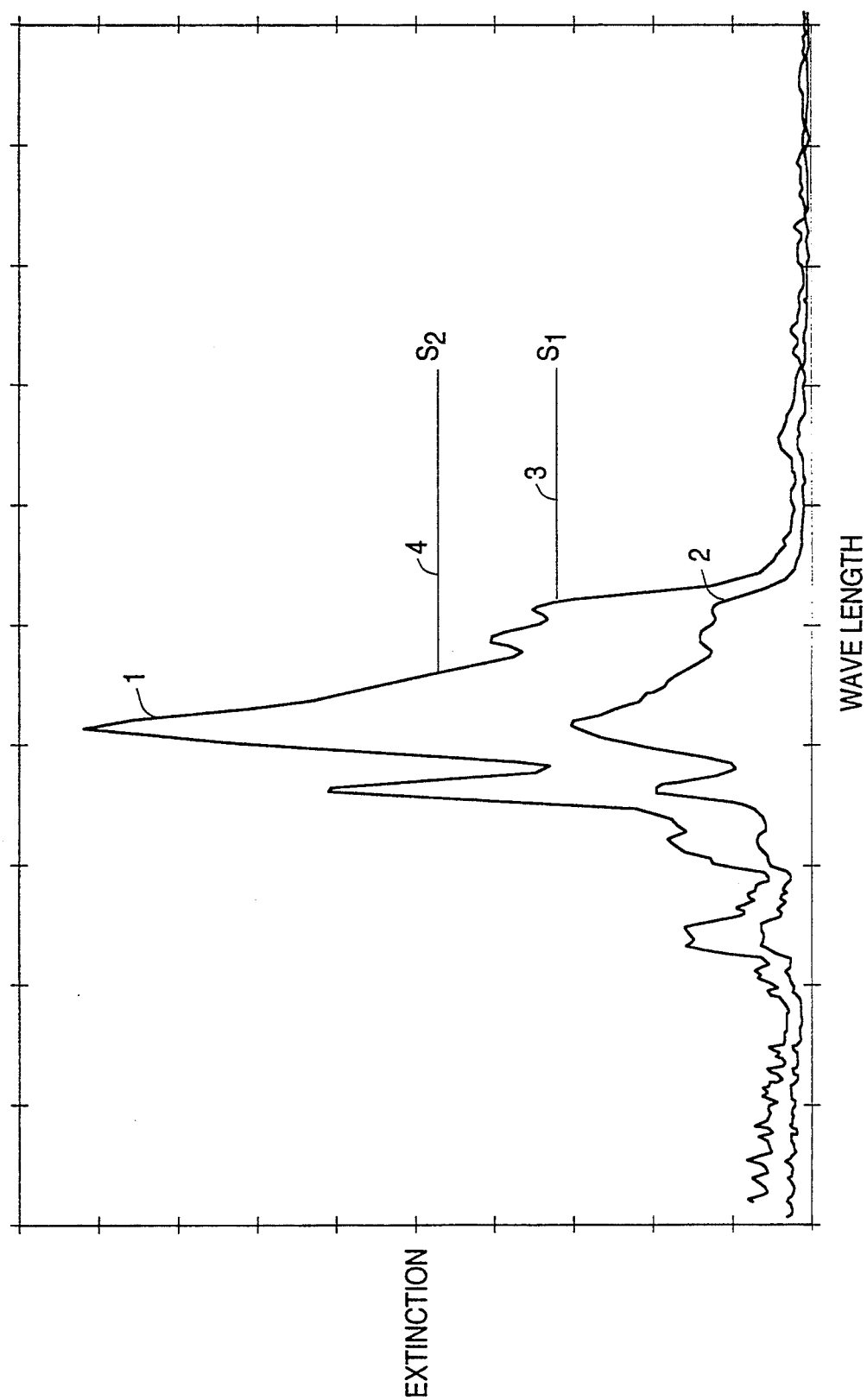
FIG. 1 is the different limonene concentrations in a soft drink or a domestic cleaning agent with the thresholds $S_3$ and $S_4$.
Figure 2:
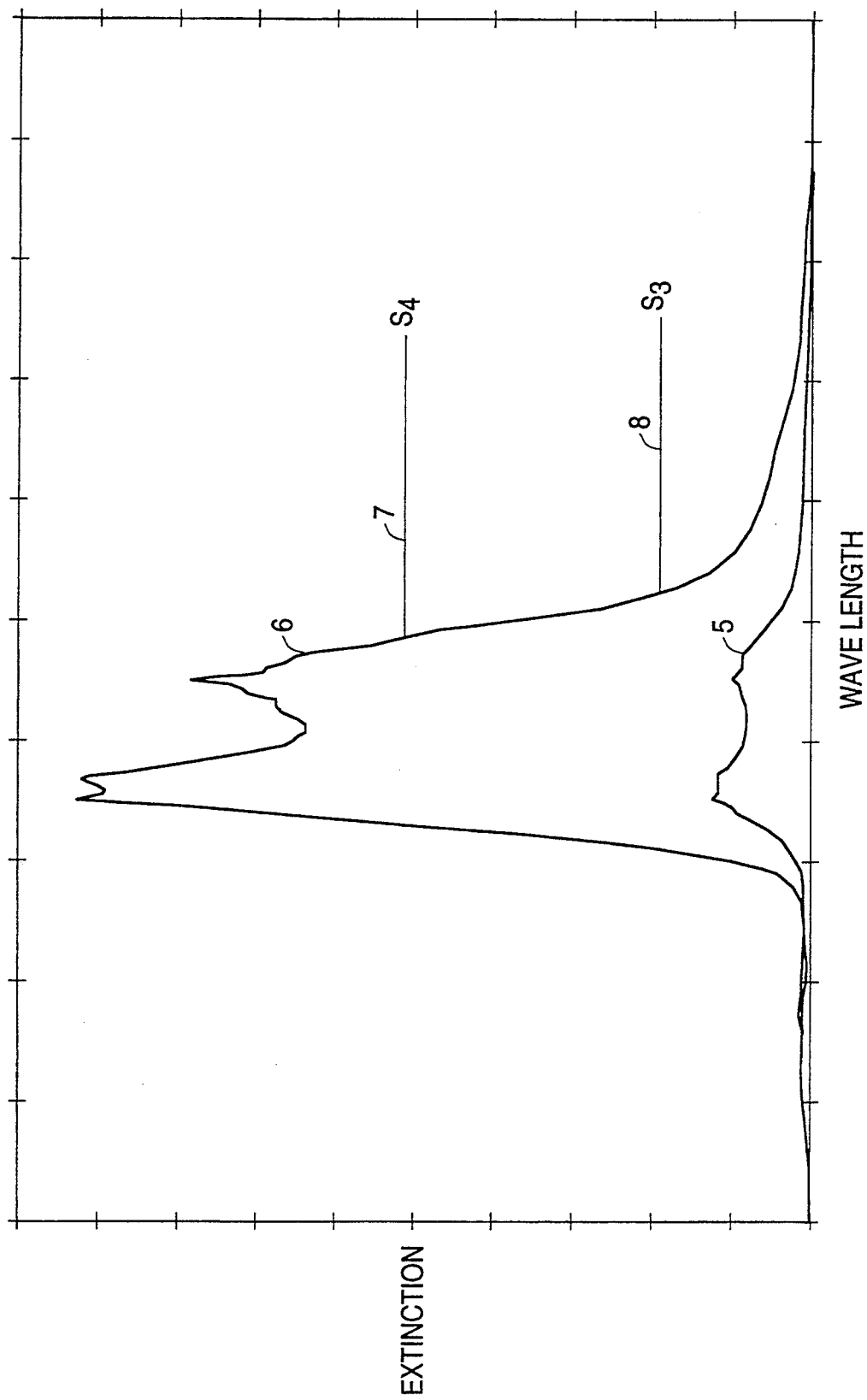
FIG. 2 is the different ethanol concentrations in a fermented soft drink or a high percentage alcoholic liquor with the thresholds $S_3$ and $S_4$.

FIG. 1 shows a spectral distribution of the gaseous phase of limonene in a multipurpose cleaner (1) and a soft drink (2) obtained with an arrangement according to U.S. patent application No. 905,470. It can be seen that the limonene concentration in the multipurpose cleaner (1) is much higher than in the soft drink (2). As a result of the inventive introduction of the thresholds $S_1$ (3) and $S_2$ (4) limonene-camouflaged pollutants (1) can be discharged, whereas limonene-mixed soft drinks (2) can remain in the bottle/container. The threshold $S_1(3)$ is such that it is above the limonene concentration of all soft drinks. The threshold $S_2$ (4) is fixed in such a way that the limonene concentration of the particular cleaning agent (1) etc. is above the threshold $S_2(4)$. This also applies with respect to the ethanol concentrations of a fermented soft drink (5) and a high percentage alcoholic liquor (6) shown in FIG. 2. As the liquor is above the threshold $S_4$ (7), the associated bottle is discharged. However, the bottle with the fermented soft drink remains in the filling line, because the maximum ethanol concentration (5) is below the threshold $S_3$ (8).

Figure 3:
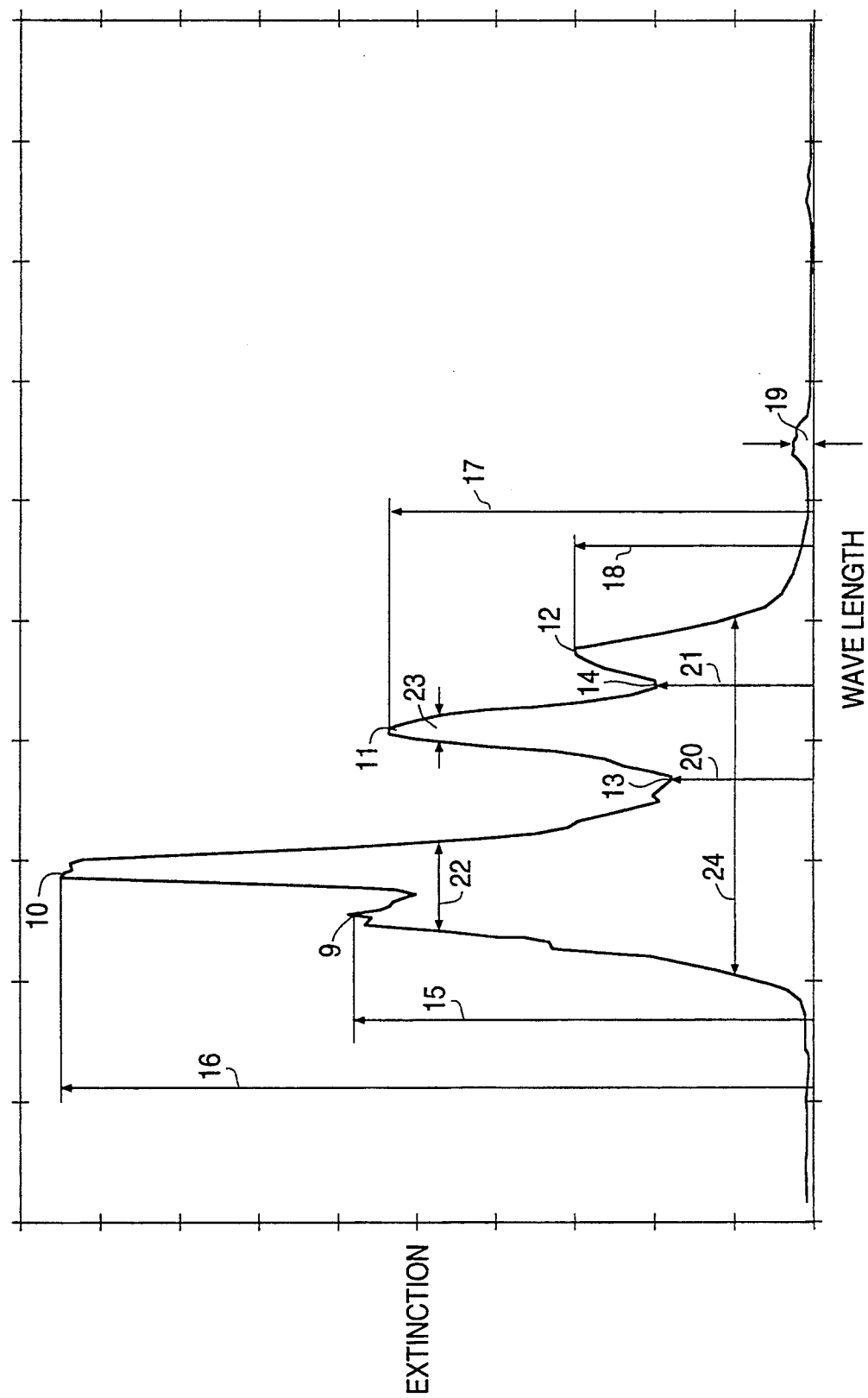
FIG. 3 is the selective substance identification over selected spectral parameters.

FIG. 3 shows the substance identification according to the invention over selected spectral parameters using the example of the pollutant pentachlorophenol. For this purpose a check is initially made as to establish which substance, contained in a library, has maximum (9,10,11,12) or minima (13,14) at the same wavelengths as the actually determined substance. A check is then made as to whether the ratios of the relative maxima (15,16,17,18,19), e.g. (15):(16), (15):(17), (15):(18), (15):(19), (16):(17), (16):(18), (16):(19), (17):(18), (17):(19), (18):(19) coincide within certain predeterminable limits with the quotients filed in the memory. Finally a check is made as to whether the ratios of the amplitudes (20,21) of the minima, i.e. (20,21) in the predetermined limits coincide with the stored quotients. To further increase identification certainty the corresponding ratios can be formed from the minimum and maximum amplitude values. Further characteristic features can be gathered from the half-intensity widths (22,23) and the base width (24), e.g. at 10% of the maximum amplitude.

Figure 4:
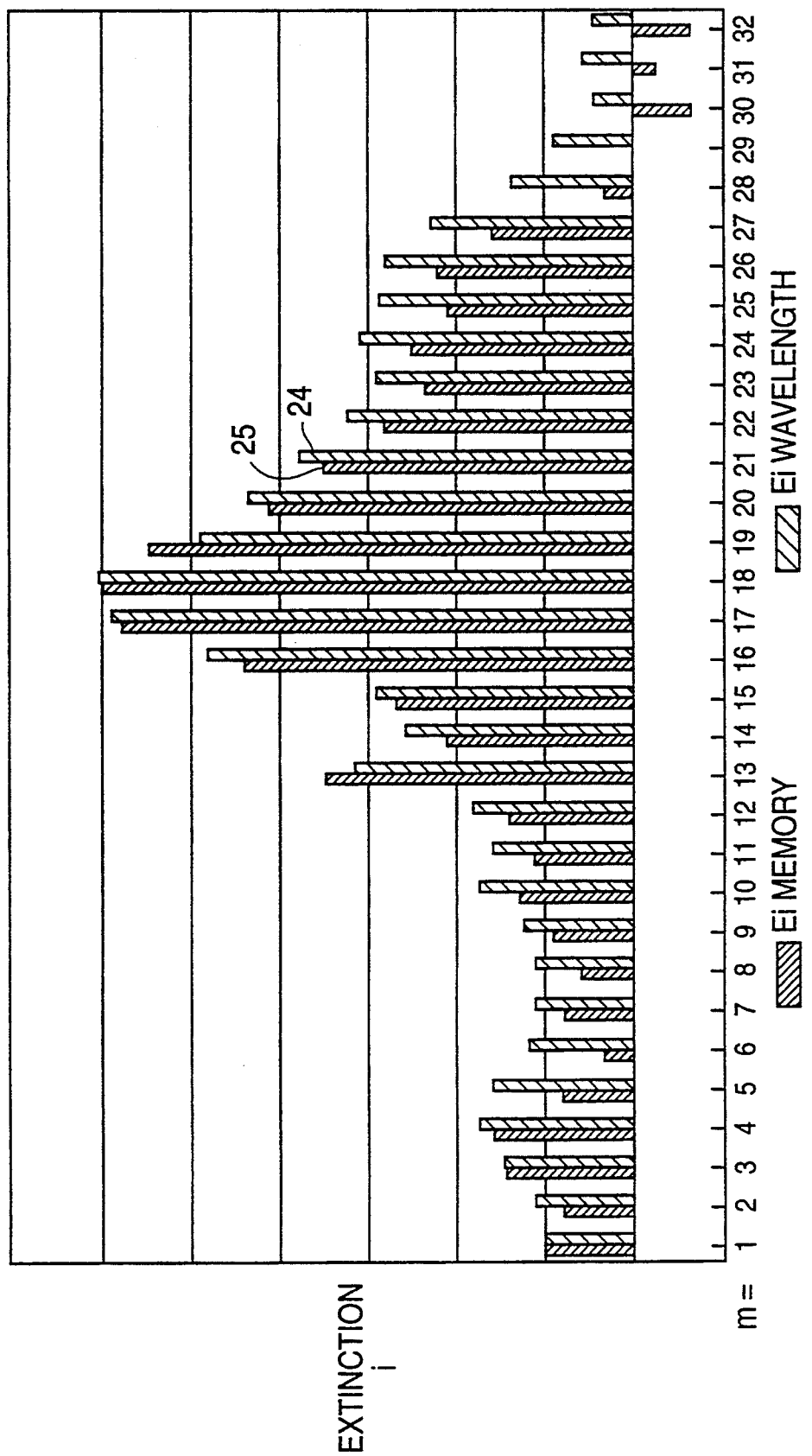
FIG. 4 is the selective substance identification over the sum of the standard deviations and the selective substance identification over the sum of the differences.

According to the invention and FIG. 4 the sum of the standard deviations or the sum of the absolute values of the differences between the actual spectrum (24) and the spectra (25) filed in the memory is formed. FIG. 4 shows as an example a spectrum (25) for limonene from the memory as compared with the actually measured limonene spectrum (24). The formation of the sum of the standard deviations $$\sum_{i=1}^{m} (E_i \text{ memory} - E_i)^2 \text{ or}$$

sum of the differences $$\sum_{i=1}^{m} (E_i \text{ memory} - E_i)^2$$

of both spectra in both cases leads to minimum values of the sums or totals compared with the cases in which spectra of different substances are compared and in which:

$E_{76} = \delta_t \cdot 1 \cdot n_t =$ extinction
$\delta_t =$ absorption coefficient
$1 =$ optical wavelength
$n_t =$ number of pollutant molecules/cm$^3$.

Figure 5A:
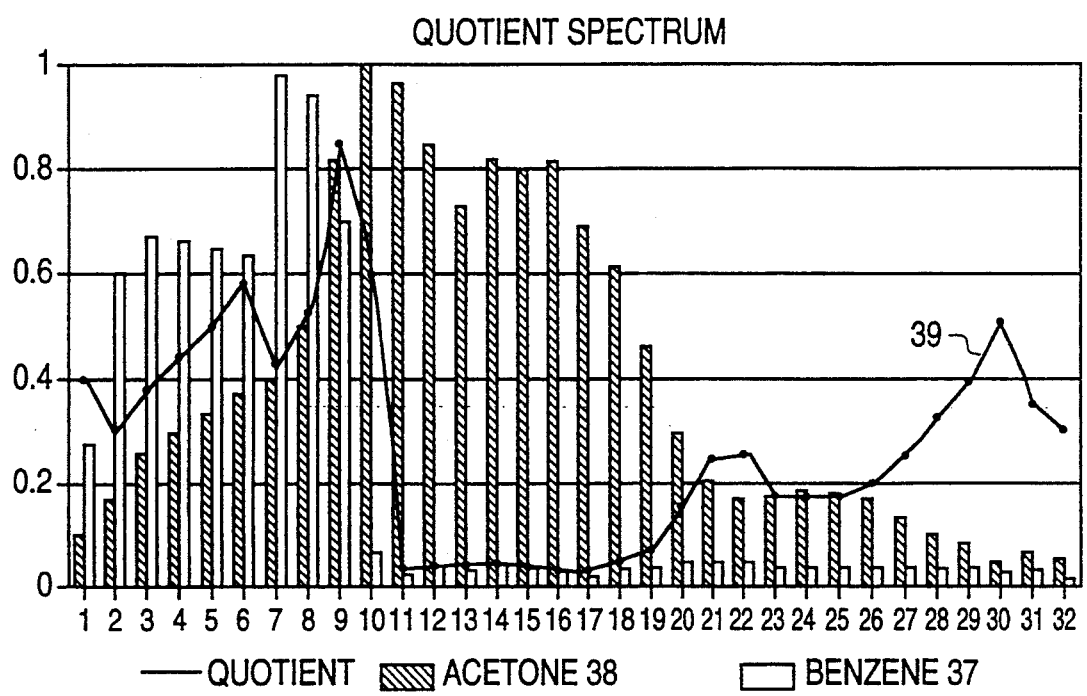
FIG. 5a is a quotient formation between the spectra of different substances.
Figure 5B:
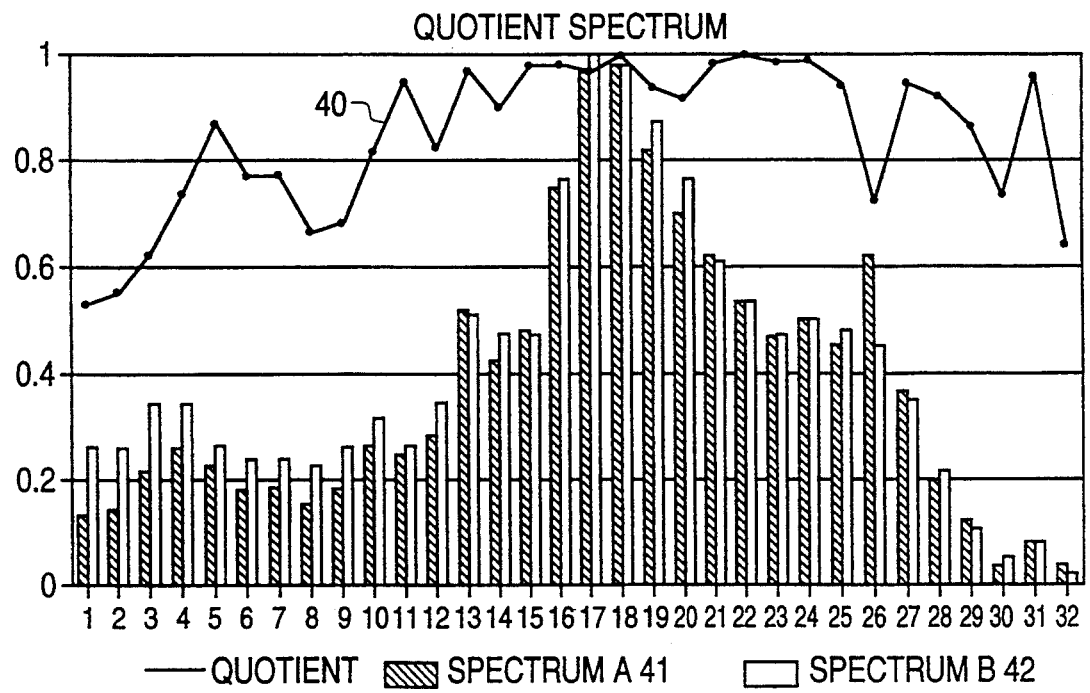
FIG. 5b is a quotient formation between spectra of identical substances.

FIG. 5a shows the result of quotient formation (39) between spectra of different substances, in this case benzene (37) and acetone (38), FIG. 5b gives the corresponding result of quotient formation of a spectrum from the memory (41) and an actual spectrum (42) for the same substances, such as e.g. limonene. According to the invention, for simple evaluation purposes the total of the individual values of the quotient spectrum is formed, the maximum sum characterizing the identical substance.

Figure 6:
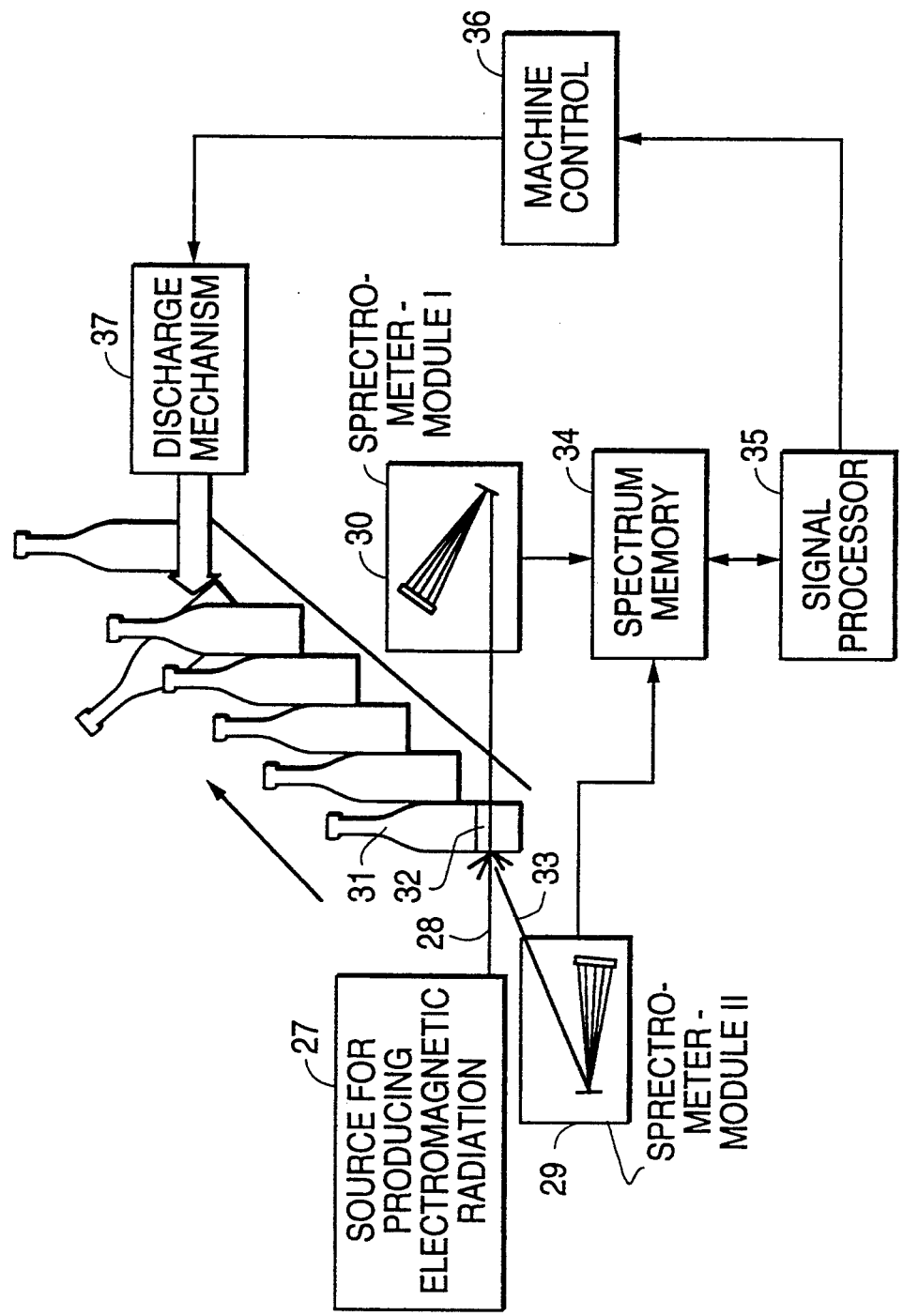
FIG. 6 is a diagram of the overall arrangement of the system according to the invention.

The overall system according to the invention is shown in FIG. 6. A source (27) for producing electromagnetic radiation in the ultraviolet, infrared and microwave range irradiates the bottle (31)/container to be tested in accordance with the beam path (28) or the beam path of the scattered or reflected beam (33). The changes in the spectral composition of the radiation brought about by the contents (32) or the pollutants are analysed by the spectrometer modules I,II (30,29). The resulting spectra are comDared on-line by a signal processor (35) with the known spectra stored in a spectrum memory (34). If the marginal conditions for a bottle/container discharge are fulfilled, by means of an instruction to the machine control (36) the discharge mechanism (37) is activated and the bottle is discharged.

I claim:

1. A method for identifying and differentiating between harmful substances and content substances in bottles or containers using absorption, reflection and scattering of electromagnetic waves from UV to a microwave range by evaluating substance-specific spectra, the method comprising the steps of:
   analyzing the substance in the bottle or container spectroscopically,
   forming a difference between measured intensity values and intensity values of comparison spectra stored in a memory;
   forming a sum of a positive function of calculated differences of the measured intensity values and the intensity values of the comparison spectra,
   comparing the formed sum with at least one preset threshold value, and
   further processing the bottle or container if the formed sum is less than the threshold value or eliminating the bottle or container if the formed sum is less than the at least one preset threshold value or eliminating the bottle or container if the formed sum is above the at least one preset threshold value.

2. A method according to claim 1, further comprising forming a sum of root mean squares of differences of said intensity values as the sum of the positive function of the calculated differences.

3. A method according to claim 1, wherein a sum of positive or absolute differences of said intensity values are formed as the sum of a positive function of the calculated differences.

4. A method according to claim 1, wherein the step of analyzing includes determining the content substance of the bottle or container by determining positions of a relative amplitude maxima on a wavelength scale of a spectrum to be measured and comparing the determined positions of the relative amplitude maxima with spectra stored in the memory.

5. Method according to claim 1, wherein the step of analyzing includes determining the content substance of the bottle or the container by determining positions of relative amplitude minima on a wavelength scale of a spectrum to be measured and comparing the determined positions of relative amplitude minima of spectra stored in the memory.

6. A method according to claim 1, wherein the step of analyzing includes determining the content substance of the bottle or container by determining positions of relative amplitude maxima and amplitude minima on a wavelength scale of a spectrum to be measured and comparing the determined positions with positions of relative amplitude maxima and amplitude minima of spectra stored in the memory.

7. A method according to claim 1, further comprising determining widths of peaks of measured spectra and comparing the determined widths with corresponding widths of prestored spectra of known substances.

8. A method according to claim 7, wherein said widths of said peaks are half-value widths.

9. A method according to claim 1, further comprising determining quotients of the measured intensity values and intensity values stored in a memory of several spectral forming some of the determined quotients of the measured intensity values and the intensity values of a particular spectrum of the stored spectra, and identifying the substance with whose stored spectrum the measured spectrum provides the largest sum value.

10. A method for identifying and differentiating between harmful substances and content substances in bottles or containers using absorption, reflection, and scattering of electromagnetic waves from UV to a microwave range by evaluating substance-specific spectra, the method comprising the steps of:
    measuring an absolute maximum amplitude of a spectrum;
    comparing the measured absolute maximum amplitude with a first threshold value;
    further processing the bottle or container if the measured absolute maximum amplitude is below said first threshold;
    comparing the measured absolute maximum amplitude with a second intensity threshold value; and
    eliminating the bottle or container if the measured absolute maximum amplitude is above said second threshold value.

11. A device for identifying and differentiating between harmful substances and content substances in bottles and containers using absorption, reflection, and scattering of electromagnetic waves from UV to a microwave range by evaluating substance-specific spectra, the device comprising:
    a conveyor line for conveying bottles or containers;
    an ejection device associated with said conveyor line for selectively eliminating bottles or containers from the conveyor line;
    a radiation source including at least one spectrometer for irradiating the bottles or containers;
    a spectrometer memory for storing given spectra of possible content substances of the bottles or containers;
    a signal processor for comparing measured spectra with one of a given spectra and given threshold values; and
    a comparison device connected with a control unit for actuating the ejection device in dependence upon output signals provided by the signal processor.

12. Device according to claim 11, wherein said signal processor is adapted to form differences between measured intensity values and prestored intensity values of prestored spectra and to form sums of positive functions of said differences.

13. Device according to claim 11, wherein said signal processor is adapted to form quotients of measured intensity values and prestored intensity values of prestored spectra and to form sums of positive functions of said differences.

14. Device according to claim 11, wherein said signal processor is adapted to compare measured positions of at least one amplitude maxima and amplitude minima with prestored amplitude maxima and prestored amplitude minima of prestored spectra.

15. Device according to claim 11, wherein said signal processor is adapted to determine and compare widths of peaks of measured spectra and prestored spectra.

16. Device according to claim 15 wherein said widths are half-value widths of said peaks of the measured spectra and prestored spectra.

* * * * *